United States Patent [19]

Hendriksen

[11] Patent Number: 5,059,739

[45] Date of Patent: Oct. 22, 1991

[54] HYDROGEN CHLORIDE-FREE CATALYST SYSTEM FOR DIMERIZING AND CODIMERIZING OLEFINS

[75] Inventor: Dan E. Hendriksen, Kingwood, Tex.

[73] Assignee: Exxon Chemical Patents Inc., Linden, N.J.

[21] Appl. No.: 429,877

[22] Filed: Oct. 31, 1989

[51] Int. Cl.$^5$ ............................ C07C 2/24; B01J 31/00
[52] U.S. Cl. ..................................... 585/513; 502/104; 502/117; 585/521; 585/527
[58] Field of Search ....................... 585/513, 521, 527; 502/104, 117

[56] References Cited

U.S. PATENT DOCUMENTS

| | | |
|---|---|---|
| 3,784,629 | 1/1974 | Maly et al. |
| 3,784,630 | 1/1974 | Maly et al. ............................ 585/513 |
| 3,784,631 | 1/1974 | Menapace et al. ................... 585/513 |
| 3,790,544 | 2/1974 | Maertens et al. .................... 502/117 |
| 3,813,453 | 5/1974 | Wideman ............................. 502/117 |
| 3,897,512 | 7/1975 | Brown et al. ........................ 502/117 |
| 3,903,193 | 9/1975 | Maly et al. .......................... 502/117 |
| 4,073,820 | 2/1978 | Wang et al. ......................... 585/645 |

OTHER PUBLICATIONS

Menapace et al., "Changing the Reaction Paths of a Metathesis Catalyst", Journal of Organic Chemistry, vol. 40, p. 2983 (1975).

Menapace et al., "Common Intermediates in Metathesis and Dimerization Reactions", ACS Div. of Petroleum Chemistry, Preprints, vol. 19, pp. 150–153, No. 1.

*Primary Examiner*—Curtis R. Davis
*Attorney, Agent, or Firm*—Linda K. Russell

[57] ABSTRACT

A substantially hydrogen chloride-free active catalyst system for dimerization and codimerization of alpha-olefins. The catalyst system includes, as one catalyst, a complex of a tungsten salt and an aniline, and, as a second catalyst, an alkyl aluminum halide.

38 Claims, No Drawings

HYDROGEN CHLORIDE-FREE CATALYST SYSTEM FOR DIMERIZING AND CODIMERIZING OLEFINS

BACKGROUND OF THE INVENTION

1. Field of the Invention

This invention relates to a process utilizing a substantially hydrogen chloride-free active catalyst system for dimerizing and codimerizing alpha olefins. This invention further relates to the active catalyst system and to the process for preparing this system.

2. Description of Material Information

Olefin dimerization and codimerization processes are known in the art.

Such processes include those which utilize catalysts prepared from tungsten compounds, anilines, and alkyl aluminum halides. Among these processes are those disclosed in U.S. Pat. Nos. 3,784,629, 3,784,630, and 3,784,631. These patents disclose dimerization and codimerization processes employing catalyst systems comprising at least one organometallic compound, at least one amine ligand, and the reaction product of at least one tungsten salt with at least one acidic compound (U.S. Pat. No. 3,784,629); at least one phenolic compound (U.S. Pat. No. 3,784,630), and at least one diketone (U.S. Pat. No. 3,784,631).

U.S. Pat. Nos. 3,813,453, 3,897,512, and 3,903,193 disclose catalyst systems comprising tungsten salts, anilines, and aluminum alkyl halides. Various ranges for the relative proportions of catalyst components are disclosed in these patents. These ranges, given as molar ratios, are listed in Table I.

TABLE I

| U.S. Pat. No. | Al | Molar Ratio W | N |
|---|---|---|---|
| 3,784,629 | 4–40 | 1 | 3–1 |
| 3,784,630 | 4–40 | 1 | 3–1 |
| 3,784,631 | 4–40 | 1 | 3–1 |
| 3,813,453 | 5–200 | 1 | 3–1 |
| 3,897,512 | 3–50 | 1 | 4–1 |
| 3,903,193 | 5–100 | 1 | 0.5–2.5 |

There is no indication in any of these references that the processes shown therein are actually operative throughout the entire range of these component proportions. In particular, there is no showing of operability for Al:W ratios at the lower ends of these ranges.

For instance, in each of U.S. Pat. Nos. 3,784,629, 3,784,630, and 3,784,631, the sole example utilizes an Al:W molar ratio of 10:1. The example of U.S. Pat. No. 3,813,453 utilizes an Al:W molar ratio of 2.5:0.031, or approximately 80.6:1, while the U.S. Pat No. 3,903,193 examples show molar ratios of 20:1 and 30:1. Significantly, in U.S. Pat. No. 3,897,512, the lowest Al:W molar ratio shown in the examples is 10:1, although the disclosed ranges provide for a lower limit of 3:1.

Two additional publications pertaining to such catalyst systems are MENAPACE et al., "Changing the Reaction Paths of A Metathesis Catalyst", *Journal of Organic Chemistry*, Vol. 40, p. 2983 (1975), and MENAPACE et al., "Common Intermediates in Metathesis and Dimerization Reactions" ACS Div. of Petroleum Chemistry, Preprints, Vol. 19, pp. 150-153, No. 1, February (1974).

Both articles show a plot of propylene dimerization activity against Al:W ratio for an ethylaluminum sesquichloride cocatalyst which shows no dimerization activity at Al:W=3:1. The former article, at p. 2984, does show a plot for the conversion of propylene with an ethylaluminum dichloride cocatalyst having an Al:W ratio in the range of 0.5:1 to 3:1. In this range, the article indicates that metathesis and dimerization occur simultaneously.

However, it is further specified therein that this is not propylene dimerization; rather, what is occurring is dimerization of the ethylene resulting from propylene metathesis, and codimerization of the ethylene with propylene. As specifically stated at the end of the paragraph spanning the first and second columns of page 2984, increasing the Al:W ratio results in predomination of dimerization.

As to the proportion of Al to W required to render the catalyst system operative, it is noted that none of these references discloses or suggests the removal of the hydrogen chloride, resulting from formation of the complex from the tungsten salt and the aniline, from the catalyst solution. It is the presence of this hydrogen chloride, either in the catalyst solution or chemically combined, which necessitates the higher molar ratio of aluminum to tungsten.

The catalyst formation process of the present invention provides for the removal, or evolution, from the catalyst solution of the hydrogen chloride resulting from the formation of the complex between the tungsten compound and the aniline. As a result, an active catalyst system for olefin dimerization (with no metathesis) can be formed with a molar ratio of Al:W as low as 2:1.

SUMMARY OF THE INVENTION

This invention pertains to a process for preparing an active catalyst system substantially free of hydrogen chloride. In this process, a tungsten salt and an aniline of the formula

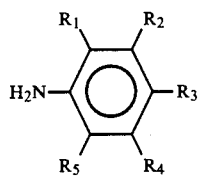

wherein each of $R_1$–$R_5$ is selected from the group consisting of hydrogen, halogens, and hydrocarbon groups, are reacted in solution to form a complex of the tungsten salt and aniline. Substantially all of the hydrogen chloride produced in this reaction is removed from the solution during the course of the reaction. After formation of the tungsten and aniline complex, an alkyl aluminum halide is added to the solution to form the active catalyst system of the invention.

As one means of removing hydrogen chloride from the solution during the reaction of the tungsten salt and aniline, the reaction is performed in the presence of an inert gas stream, and preferably entirely under an inert atmosphere in order to exclude moisture in particular and also oxygen.

In a specific embodiment of the process of preparing the active catalyst system, a solution comprising the tungsten salt and a solvent are subjected to reflux and stirring. During this reflux and stirring, a composition comprising aniline is added to, and an inert gas stream is maintained in the presence of, this solution. The refluxing and stirring is halted and, thereafter, the alkyl aluminum halide is added to the solution to form the active catalyst system.

In a preferred embodiment, the relative proportions of the alkyl aluminum halide and tungsten utilized in the catalyst system preparation process are such that the molar ratio of aluminum to tungsten is about 5:1 or less; more preferably this ratio is about 3:1 or 5:1, which is dependent upon which alkyl aluminum halide is used in the process of preparing the catalyst system. Further, the relative proportions of aniline and tungsten salt utilized in the process are such that the molar ratio of aniline to tungsten is about 1:1.

A preferred tungsten salt suitable for use in the process of preparing the active catalyst system is tungsten hexachloride. The aniline may be at least one of the group including 2,4,6-trichloroaniline, 2,6-dimethylaniline, 2,4,6-tribromoaniline, and 2,6-diisopropylaniline. The alkyl aluminum halide may be at least one of the group including ethylaluminum dichloride, diethylaluminum chloride, and ethylaluminum sesquichloride. Any suitable solvent may be employed in this process of preparing the active catalyst system. One such solvent is chlorobenzene.

The invention is also directed to a substantially hydrogen chloride-free active catalyst system prepared by the process of the present invention, as described above. The substantially hydrogen chloride-free catalyst system of the present invention comprises one catalyst consisting of the tungsten salt and aniline, and a second catalyst comprising the alkyl aluminum halide.

Preferably, the proportions of alkyl aluminum halide and tungsten salt present in the active catalyst system of the invention are such that the molar ratio of aluminum to tungsten is about 5:1 or less. The most preferred ratio is 3:1 or 5:1, which is dependent upon which alkyl aluminum halide is used in the process of preparing the catalyst system. Further, the relative proportions of the aniline and the tungsten salt present in the system are preferably such that the molar ratio of aniline to tungsten is about 1:1.

The tungsten salt of the active catalyst system may be tungsten hexachloride. The aniline may be at least one of the group including 2,4,6-trichloroaniline, 2,6-dimethylaniline, 2,4,6-tribromoaniline, and 2,6-diisopropylaniline. The alkyl aluminum halide of the active catalyst system may be at least one member from the group including ethylaluminum dichloride, diethylaluminum chloride, and ethylaluminum sesquichloride.

Preferably, the active catalyst system of the present invention further includes a solvent for the tungsten salt - aniline complex and for the alkyl aluminum halide with chlorobenzene being a particular suitable solvent.

The present invention is further directed to a process for dimerizing an alpha-olefin, or codimerizing two dissimilar alpha-olefins. In this process, the alpha-olefin or alpha-olefins are contacted with the substantially hydrogen chloride-free active catalyst system of the present invention, as described above.

A preferred alpha-olefin for dimerizing in the process of this invention is propylene. Preferably, the alkyl aluminum halide of the active catalyst system used in this dimerization of propylene is ethylaluminum dichloride, and the relative proportions of ethylaluminum dichloride and the tungsten salt present in the system are such that the molar ratio of aluminum to tungsten is about 5:1 or less.

The process of the present invention may also be utilized to dimerize ethylene to selectively yield 1-butene, and to codimerize ethylene with 1-butene to selectively yield 3-methyl-1-pentene.

DESCRIPTION OF PREFERRED EMBODIMENTS

The dimerization and codimerization process of this invention is suitable for olefins of the formula:

where there may be branching in the R group, such as 3-methyl-1-butene, particularly those having 2-8 carbons, although not particularly suitable for 2-methyl-1-butene and isobutene. The process is preferred for alpha-olefins, particularly linear alpha olefins, including both straight and branched olefins. Ethylene may be dimerized to yield selectively 1-butene. Propylene may be dimerized to yield selectively 2,3-dimethyl-1-butene which, in turn, may be used directly as an intermediate, or instead may be isomerized with an acid catalyst to yield 2,3-dimethyl-2-butene, also known as tetramethylethylene (TME). TME is useful as an intermediate in the production of certain fragrances and pesticides, as well as in the preparation of pinacol and pinacolone.

Inasmuch as the catalyst of the present invention isomerizes the terminal olefins to internal olefins very slowly, linear terminal olefins of longer chain length may also be dimerized.

As to codimerization, the process of the invention is especially suitable for codimerizing ethylene with other linear terminal olefins. In this context, linear terminal olefins are understood to have the structure R—CH=CH$_2$, with R comprising a linear or branched alkyl group.

The components of the catalyst system of the present invention comprise at least one tungsten compound, which is preferably a tungsten salt, at least one aniline, and at least one alkyl aluminum halide.

The most preferred tungsten salt to be used with the catalyst system of the present invention is tungsten hexachloride. Also suitable are tungsten oxytetrachloride, tungsten pentabromide, and tungsten oxytetrabromide.

The anilines suitable for the catalyst system of the present invention are those of the formula

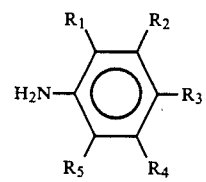

wherein, $R_1$–$R_5$ are hydrogen, halides, or alkyl groups. The substituted anilines are preferred, and 2,6-dimethylaniline, 2,6-diisopropylaniline, 2,4,6-tribromoaniline, and 2,4,6trichloroaniline are more preferred, with 2,4,6trichloroaniline being the most preferred, although unsubstituted aniline may be used.

The alkyl aluminum halides suitable for the catalyst system of the present invention have a general formula $R_n Al Cl_{3-n}$ where n is less than or equal to about 2, and preferably is selected from the group consisting of 1, 1.5 and 2, and R is an alkyl group containing 1-10 carbon atoms. The alkyl aluminum halide is preferably a member selected from the group consisting of ethylaluminum sesquichloride, ethylaluminum dichloride, and diethylaluminum chloride.

In dimerizing propylene, employing ethylaluminum dichloride as the alkyl aluminum halide of the catalyst system, and maintaining the catalyst system Al:W equivalent ratio at 3:1 or less, greatly reduces the selectivity to 2-methyl-1-pentene. Such selectivity is of great benefit because this hexene isomer is difficult to separate by distillation from the preferred product, i.e., 2,3-dimethyl-1-butene, and is, therefore, an undesirable product; moreover, 2-methyl-2-pentene, which is the internal isomer of 2-methyl-1-pentene, is difficult to separate from 2,3-dimethyl-2-butene, another product of the dimerization. Accordingly, for this embodiment of the dimerization process, an additional advantage is realized from the selectivity of the catalyst system of the invention at a lower Al:W ratio.

The catalyst system further includes a suitable solvent for these components, and in which the complexing of the tungsten salt and aniline takes place. In general the solvent for the reaction between the tungsten salt and the substituted aniline must be one in which these species and the hydrogen chloride-free product dissolve and which does not itself react with any of these three species, and should be dry. Suitable solvents are chlorobenzene, 1,2-dichlorobenzene, and benzene, with chlorobenzene being preferred.

Preparation of the Catalyst

The preparation of the catalyst in accordance with the present invention is preferably performed in two steps. In the first step, the reaction between the tungsten hexachloride and the 2,4,6-trichloroaniline (1:1 mole ratio) results in the evolution of 2 moles of hydrogen chloride per mole of tungsten. In the second step, an appropriate amount of alkylaluminum chloride is added to the solution of the resulting product.

Although not wishing to be bound by any particular theory, it is believed that 2 moles of hydrogen chloride are evolved for every mole of tungsten hexachloride so that the reaction appears to conform to the following chemical equation:

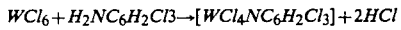

$$WCl_6 + H_2NC_6H_2Cl_3 \rightarrow [WCl_4NC_6H_2Cl_3] + 2HCl$$

Notwithstanding the indicated composition, the precise structure of the product written within the brackets is not known.

Despite attempts which have been made to produce this complex by removing hydrogen chloride by other means, none has been found to be successful in preparing the complex; therefore, it is doubtful that all of the hydrogen chloride had been successfully removed by these attempts.

Therefore, although the precise nature of the product complex is not known, it is believed to be distinguished from the species obtained without removing the hydrogen chloride. Whereas the former is soluble in the chlorobenzene solvent at room temperature, the latter is not. Also, the two complexes exhibit a different color.

In the preparation of the complex, the proportion of aniline to the tungsten salt which is suitable for purposes of the present invention is within the range of 0.5 to 1.5, with 0.8 to 1.2 being preferred, and 0.95 to 1.05 being most preferred.

The reaction is conducted at a temperature of at least about 75° C. (wherein the boiling point of benzene is 80° C.); and preferably the temperature is within the range of 75° C. to about 200° C. The reaction pressure is preferably ambient (1 atmosphere) but may be below atmospheric pressure.

The reaction of the tungsten salt is important; the rate of addition of aniline should be sufficiently slow enough to allow the hydrogen chloride formed from the reaction to be substantially evolved from the solution before an additional amount of aniline is added.

It has been observed that a sufficient amount of alkylaluminum chloride should be added so as to be present in an Al/W ratio of about 2, particularly when used with a diethyl aluminum cocatalyst. In contrast, ethylaluminum sesquichloride and ethylaluminum chloride added in an amount to have an Al/W ratio of 2 does not result in any reaction, while an Al/W ratio of 3 shows good results. Accordingly, when using a dialkylaluminum chloride, a molar ratio of Al/W in the range of 2–50 should be used, with a most preferred range being 2–5. When the cocatalyst used is alkylaluminum sesquichloride or alkylaluminum dichloride, a range of 3–50 is suitable, with a more preferred range of 3–5.

The reaction temperature for the addition of the cocatalyst suitable for purposes of the present invention is ambient, but may range as low as 0° C. or below.

Dimerization or Codimerization

In this embodiment, the ratio of olefin to tungsten should be such that a catalytic amount of the tungsten complex is used. The reaction may be run in either a batch or a continuous manner. The reaction pressure is normally the pressure generated by the olefin at the reaction temperature, although the pressure may be increased with an inert gas. The reaction temperature may range from about 40° C.–100° C., with 50° C.–80° C. being preferred. The reaction or residence time may be within the range from about 5 minutes to about 3 hours, with 0.5–2.0 hours being preferred.

EXAMPLES

In the following examples, the catalyst system was prepared in accordance with the process of the invention under conditions which favor removal of evolved HCl. In this regard the catalyst is prepared in the presence of a stream of inert gas, and preferably nitrogen. Unexpectedly, it has been discovered that if the catalyst system is prepared simply under a nitrogen atmosphere, the HCl is not removed from the system. Thus, for each volume of HCl gas evolved per minute, an inert or nitrogen gas stream having a flow within the range of 1 to about 100 volumes per minute has been found to be suitable for this purpose with 5 to about 20 volumes per minute being preferred. The catalyst thus formed was employed in the olefin dimerization in these Examples.

Specifically, as to catalyst system formation, in a glove box, 0.33 g. of tungsten hexachloride was placed in a 3 neck flask with a magnetic stirring bar, and dissolved in 10 ml. of dry chlorobenzene. One equivalent of 2,4,6-trichloroaniline (0.149 g.) was placed in a dropping funnel and dissolved in 5 ml. of dry chlorobenzene. The resulting tungsten hexachloride solution was refluxed and rapidly stirred; during the refluxing and stirring, the trichloroaniline solution was added dropwise; during this addition, a flow of nitrogen was maintained, entering the reaction flask and exiting up the reflux condenser so as to remove the evolution of hydrogen chloride which resulted from the reaction between 2,4,6-trichloroaniline and the tungsten hexachloride.

The results shown are selectivities in the $C_6$ products, conversion of propylene, and total reaction time.

| | |Al/W | conv |(%) | time |(hrs) | EtAlCl$_2$ Cocatalyst Selectivity in $C_6$ Products |||||||
|---|---|---|---|---|---|---|---|
| | | | | |4MP1 |4MP2 |2MP1 |2MP2 |DMB0 |DMB1 |DMB2 |
| Example 1 | 1 | 0 | 1.3 | — | — | — | — | — | — | — |
| Example 2 | 2 | 0 | 0.5 | — | — | — | — | — | — | — |
| Example 3 | 3 | 85 | 1.0 | 5 | 12 | 1 | 1 | 3 | 67 | 10 |
| Example 4 | 5 | ~85 | 0.5 | 2 | 7 | 4 | 1 | 1 | 81 | 3 |
| Example 5 | 11.5 | 89 | 0.5 | 2 | 6 | 6 | 1 | 1 | 81 | 2 | where:
4MP1 = 4-methyl-1-pentene
4MP2 = 4-methyl-2-pentene
2MP1 = 2-methyl-1-pentene
2MP2 = 2-methyl-2-pentene
DMB0 = 2,3-dimethylbutane
DMB1 = 2,3-dimethyl-1-butene
DMB2 = 2,3-dimethyl-2-butene After the dropwise addition was completed, the solution was refluxed for an additional five minutes, and thereafter allowed to cool to room temperature. The resulting solution was dark, yellow-brown, with no precipitate.

A suitable amount of alkyl aluminum chloride cocatalyst was added to the cooled solution via syringe with stirring, changing the color of the solution to dark orange-brown.

As to the dimerization reaction, each of the examples comprises a propylene dimerization which was performed by transferring the catalyst prepared above via syringe to a dry 300 ml. autoclave equipped with a stirrer and equipment for temperature control. Approximately 75 g. of polymer grade propylene was added to the autoclave from a bomb with added nitrogen pressure. The autoclave was then sealed, and rapidly heated to 60° C.

The progress of the dimerization reaction was monitored by observing the pressure decrease in the autoclave reactor as a function of time. At the time chosen for the end of the dimerization reaction, the autoclave was rapidly cooled in an ice bath to stop the reaction. The remaining propylene was vented; 10 ml. of isopropanol was added to quench the alkyl aluminum chloride, the autoclave was opened, and the contents thereof were removed. The resulting solution was analyzed by means of a gas chromatograph equipped with a capillary column.

For the following Examples, Examples 1-5, the alkyl aluminum halide utilized in the catalyst system was ethylaluminum dichloride, at the indicated Al:W ratios.

For the following Examples, Examples 6-8, the alkyl aluminum halide was ethylaluminum sesquichloride.

| | |Al/W | conv |(%) | time |(hrs) | Et$_3$Al$_2$Cl$_3$ Cocatalyst Selectivity in $C_6$ Products |||||||
|---|---|---|---|---|---|---|---|
| | | | | |4MP1 |4MP2 |2MP1 |2MP2 |DMB0 |DMB1 |DMB2 |
| Example 6 | 2 | 0 | 1.2 | — | — | — | — | — | — | — |
| Example 7 | 3 | 65 | 1.1 | 3 | 5 | 10 | 0.5 | 1 | 81 | 0.5 |
| Example 8 | 5 | 33 | 2.0 | 4 | 6 | 11 | 0.2 | 1 | 78 | 0.5 |

For the following Examples, Examples 9-11, the alkyl aluminum halide was diethylaluminum chloride.

| | |Al/W | conv |(%) | time |(hrs) | Et$_2$AlCl Cocatalyst Selectivity in $C_6$ Products |||||||
|---|---|---|---|---|---|---|---|
| | | | | |4MP1 |4MP2 |2MP1 |2MP2 |DMB0 |DMB1 |DMB2 |
| Example 9 | 2 | 45 | 1.6 | 3 | 5 | 10 | 0.2 | 1 | 80 | 0.6 |
| Example 10 | 3 | 46 | 1.6 | 3 | 5 | 11 | 0.2 | 1 | 79 | 0.4 |
| Example 11 | 5 | ~10 | 1.0 | 4 | 6 | 11 | 0.2 | 1 | 77 | 0.6 |

EXAMPLE 12

Tungsten hexachloride (992 mg., 2.5 mmole) was dissolved in 30 ml of dry chlorobenzene and 2,4,6-trichloroaniline (491 mg., 2.5 mmole) in turn was dissolved in 15 ml dry chlorobenzene, both under a nitrogen atmosphere in the absence of air and moisture. With the WCl$_6$ solution refluxing and being stirred, the 2,4,6-trichloroaniline solution was added dropwise over 15 minutes. A flow of dry nitrogen was introduced into the flask to sweep the evolved hydrogen chloride up the reflux condenser. The gas mixture was then sparged into a gas scrubbing tower containing 100 ml of 0.1 N aqueous sodium hydroxide. The gas flow exiting this vessel then entered an identical vessel to remove any residual HCl. Ten minutes after the addition of the 2,4,6-trichloroaniline was complete, the gas scrubbing towers were removed, and the contents were titrated with aqueous 0.1 N HCl to determine how much HCl had been absorbed in the aqueous NaOH from the reaction between the tungsten hexachloride and the 2,4,6-trichloroaniline.

The titration shows that 5.23 mmole of HCl had been absorbed from the gas flowing out of the reactor vessel, or 2.1 mmole HCl per mmole of WCl$_6$ reacted. The solution formed from the reaction was observed to be dark, yellow-brown, with no precipitate.

It is significant that the product of this reaction is a solution with no precipitate when the two mmoles of hydrogen chloride per mmole of tungsten are remo

EXAMPLE 13

The procedure substantially as described above with respect to Example 12 was followed, but without a flow of nitrogen to remove evolved HCl, and with a mole ratio of aniline to tungsten of 2:1. Using 2,4,6-trichloroaniline as the aniline, a quantity of yellow-green precipitate with a pale blue solution was obtained. When this procedure was modified to provide for removal of the hydrogen chloride as the reaction proceeds, however, the resultant product was observed to be a dark, burgundy-brown solution with no precipitate. It appears that the color changes from dark yellow-brown as the second equivalent of 2,4,6-trichloroaniline is added.

The change in procedure was to add the solution of 2,4,6-trichloroaniline dropwise over 15 minutes to the refluxing solution of the $WCl_6$ while a flow of nitrogen enters the flask and carries the evolved HCl up the reflux condenser.

It should be understood that although the invention has been specifically described with reference to particular means and embodiments, the foregoing description is that of preferred embodiments of the invention. Thus, the present invention is not limited to the particulars disclosed, but extends to all equivalents, and various changes and modifications may be made in the invention without departing from the spirit and scope thereof.

What is claimed:

1. A process for dimerizing an alpha-olefin or codimerizing two dissimilar alpha-olefins, said process comprising:
   contacting a member selected from the group consisting of alpha olefin and a mixture of two dissimilar alphaolefins with an active catalyst system substantially free of hydrogen chloride, said system comprising:
   (a) a complex comprising a tungsten salt and an aniline of the formula

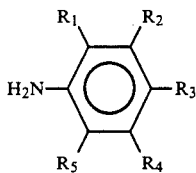

wherein each of $R_1$-$R_5$ is selected from the group consisting of hydrogen, halogens, and hydrocarbon groups; and
   (b) an alkyl aluminum halide.

2. The process as defined by claim 1 wherein said system further comprises:
   (c) a solvent for said complex and said alkyl aluminum halide.

3. The process as defined by claim 2 wherein said solvent comprises chlorobenzene.

4. The process as defined by claim 2 wherein the relative proportions of said alkyl aluminum halide and said tungsten salt present in said system are such that the molar ratio of aluminum to tungsten is about 5:1 or less.

5. The process as defined by claim 4 wherein said molar ratio of aluminum to tungsten is about 5:1.

6. The process as defined by claim 5 wherein the relative proportions of said aniline and said tungsten salt present in said system are such that the molar ratio of aniline to tungsten is about 1:1.

7. The process as defined by claim 4, wherein said aniline is a substituted aniline.

8. The process as defined by claim 7, wherein said aniline is selected from the group consisting of 2,4,6-trichloroaniline, 2,6-dimethylaniline, 2,4,6-tribromoaniline and 2,6-diisopropylaniline.

9. The process as defined by claim 4 wherein said alkyl aluminum halide is at least one member selected from the group consisting of ethylaluminum dichloride, diethylaluminum chloride, and ethylaluminum sesquichloride.

10. The process as defined by claim 4, wherein said tungsten salt is tungsten hexachloride.

11. The process as defined by claim 1, wherein said member is an alpha-olefin.

12. The process as defined by claim 11, wherein said alpha olefin is propylene.

13. The process as defined by claim 12, wherein said propylene is dimerized to result in 2,3-dimethyl-1-butene.

14. The process as defined by claim 12, wherein said alkyl aluminum halide comprises ethylaluminum dichloride.

15. The process as defined by claim 11, wherein said alpha-olefin is ethylene and is dimerized to result in 1-butene.

16. The process as defined by claim 1, wherein said member is a mixture of two dissimilar olefins.

17. The process as defined by claim 16, wherein one of said two dissimilar olefins is ethylene.

18. The process as defined by claim 17, wherein said two dissimilar olefins are ethylene and 1-butene.

19. The process as defined by claim 18, wherein ethylene and said 1-butene are codimerized to result in 3-methyl-1-pentene.

20. A process for preparing a catalyst system, substantially free of hydrogen chloride, said process comprising:
   (a) reacting, in solution, a tungsten salt and an aniline of the formula

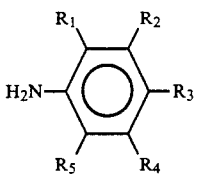

wherein each of $R_1$-$R_5$ is selected from the group consisting of hydrogen, halogens, and hydrocarbon groups, to form a complex of said tungsten salt and said aniline;
   (b) removing from said solution, during the reaction of said tungsten salt and said aniline, substantially all hydrogen chloride resulting from said reaction; and
   (c) adding an amount of an alkyl aluminum halide to said solution, after formation of said complex, to form said active catalyst system.

21. The process as defined by claim 20 wherein said tungsten salt and said aniline are reacted in the presence of an inert gas stream for removing said hydrogen chloride.

22. The process as defined by claim 21, wherein said inert gas is nitrogen.

23. The process as defined by claim 20 wherein said amount of said alkyl aluminum halide is effective to result in the presence of said alkyl aluminum halide and said tungsten salt in relative proportions such that the molar ratio of aluminum to tungsten is about 5:1 or less.

24. The process as defined by claim 23 wherein said molar ratio of aluminum to tungsten is about 5:1.

25. The process as defined by claim 24 wherein the said aniline and said tungsten salt are present in said solutions in relative proportions such that the molar ratio of aniline to tungsten is about 1:1.

26. The process as defined by claim 23 wherein said aniline is at least one member selected from the group consisting of 2,4,6-trichloroaniline, 2,6-dimethylaniline, 2,4,6-tribromoaniline, and 2,6-diisopropylaniline.

27. The process as defined by claim 23, wherein said alkyl aluminum halide is at least one member selected from the group consisting of ethylaluminum dichloride, diethylaluminum chloride, and ethylaluminum sesquichloride.

28. The process as defined by claim 23, wherein said tungsten salt is tungsten hexachloride.

29. The process as defined by claim 21 comprising:
(a) refluxing and stirring a solution comprising said tungsten salt and solvent;
(b) during said refluxing and stirring:
  (1) adding a composition comprising aniline to said solution; and
  (2) maintaining said inert gas stream in the presence of said solution;
(c) halting said refluxing and stirring; and
(d) after halting said refluxing and stirring, adding said alkyl aluminum halide to said solution.

30. An active catalyst system substantially free of hydrogen chloride, said system comprising:
(a) a complex comprising a tungsten salt and an aniline of the formula

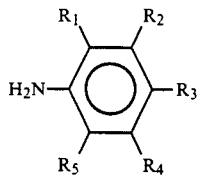

wherein each of $R_1$-$R_5$ is a member of the group consisting of hydrogen, halogens, and hydrocarbon groups; and
(b) an alkyl aluminum halide.

31. The system as defined by claim 30 further comprising a solvent for said complex and said alkyl aluminum halide.

32. The system as defined by claim 31 wherein said solvent comprises chlorobenzene.

33. The system as defined by claim 31 wherein said alkyl aluminum halide and said tungsten salt are present in said system in relative proportions such that the molar ratio of aluminum to tungsten is about 5:1 or less.

34. The system as defined by claim 33 wherein said molar ratio of aluminum to tungsten is about 5:1.

35. The system as defined by claim 34 wherein said aniline and said tungsten salt are present in said system in relative proportions such that the molar ratio of aniline to tungsten is about 1:1.

36. The system as defined by claim 33 wherein said aniline is at least one member selected from the group consisting of 2,4,6-trichloroaniline, 2,6-dimethylaniline, 2,4,6-tribromoaniline, and 2,6-diisopropylaniline.

37. The system as defined by claim 33, wherein said alkyl aluminum halide is at least one member selected from the group consisting of ethylaluminum dichloride, diethylaluminum chloride, and ethylaluminum sesquichloride.

38. The system as defined by claim 33, wherein said tungsten salt is tungsten hexachloride.

* * * * *